(12) United States Patent
Clokie et al.

(10) Patent No.: US 9,675,670 B2
(45) Date of Patent: Jun. 13, 2017

(54) SYSTEM AND METHOD FOR MULTIPHASIC RELEASE OF GROWTH FACTORS

(75) Inventors: Cameron M. L. Clokie, Toronto (CA); Sean A. F. Peel, Oakville (CA)

(73) Assignee: Induce Biologics Inc., Toronto (CA)

( * ) Notice: Subject to any disclaimer, the term of this patent is extended or adjusted under 35 U.S.C. 154(b) by 0 days.

(21) Appl. No.: 14/111,518

(22) PCT Filed: Apr. 11, 2012

(86) PCT No.: PCT/CA2012/050234
§ 371 (c)(1),
(2), (4) Date: Dec. 17, 2013

(87) PCT Pub. No.: WO2012/139223
PCT Pub. Date: Oct. 18, 2012

(65) Prior Publication Data
US 2014/0100161 A1   Apr. 10, 2014

Related U.S. Application Data

(60) Provisional application No. 61/474,049, filed on Apr. 11, 2011.

(51) Int. Cl.
| | | |
|---|---|---|
| A61K 9/52 | (2006.01) | |
| A61K 9/54 | (2006.01) | |
| A61K 38/18 | (2006.01) | |
| A61K 38/19 | (2006.01) | |
| A61K 38/22 | (2006.01) | |
| A61K 9/50 | (2006.01) | |
| A61K 9/00 | (2006.01) | |
| A61K 47/34 | (2017.01) | |
| A61K 9/16 | (2006.01) | |
| A61K 47/02 | (2006.01) | |
| A61L 27/46 | (2006.01) | |
| A61L 27/54 | (2006.01) | |
| A61K 47/10 | (2017.01) | |
| A61K 47/48 | (2006.01) | |
| A61K 9/19 | (2006.01) | |

(52) U.S. Cl.
CPC ........ *A61K 38/1875* (2013.01); *A61K 9/0024* (2013.01); *A61K 9/1611* (2013.01); *A61K 9/1641* (2013.01); *A61K 9/1682* (2013.01); *A61K 9/19* (2013.01); *A61K 9/5084* (2013.01); *A61K 38/18* (2013.01); *A61K 38/1825* (2013.01); *A61K 38/1841* (2013.01); *A61K 38/1858* (2013.01); *A61K 38/1866* (2013.01); *A61K 47/02* (2013.01); *A61K 47/10* (2013.01); *A61K 47/34* (2013.01); *A61K 47/48861* (2013.01); *A61L 27/46* (2013.01); *A61L 27/54* (2013.01)

(58) Field of Classification Search
None
See application file for complete search history.

(56) References Cited

U.S. PATENT DOCUMENTS

| | | |
|---|---|---|
| 4,761,471 A | 8/1988 | Urist |
| 4,789,732 A | 12/1988 | Urist |
| 4,795,804 A | 1/1989 | Urist |
| 4,857,456 A | 8/1989 | Urist |
| 4,877,864 A | 10/1989 | Wang et al. |
| 5,013,649 A | 5/1991 | Wang et al. |
| 5,166,058 A | 11/1992 | Wang et al. |
| 5,385,887 A | 1/1995 | Yim et al. |
| 5,618,924 A | 4/1997 | Wang et al. |
| 5,631,142 A | 5/1997 | Wang et al. |
| 6,150,328 A | 11/2000 | Wang et al. |
| 6,426,332 B1 | 7/2002 | Rueger et al. |
| 6,503,109 B1 | 1/2003 | Duffield et al. |
| 6,589,549 B2 * | 7/2003 | Shih ............... A61K 9/0024 424/426 |
| 6,593,109 B1 | 7/2003 | Israel et al. |
| 6,998,128 B2 | 2/2006 | Haggard et al. |

(Continued)

FOREIGN PATENT DOCUMENTS

| | | |
|---|---|---|
| WO | 02/070029 | 9/2002 |
| WO | WO2006093606 A1 | 9/2006 |
| WO | 2009/129464 A2 | 10/2009 |
| WO | WO2010000061 A1 | 1/2010 |
| WO | 2011/016881 | 2/2011 |

OTHER PUBLICATIONS

Johnston et al. (1992, Pharmaceutical Research 9(3):425-434).*
Azari et al., 'Therapeutic potential of bone morphogenetic proteins', Expert Opin. Investig. Drugs (2001) 10(9):1677-1686.
Barr et al., 'Comparison of the osteoinductivity of bioimplants containing recombinant human bone morphogenetic proteins 2 (Infuse) and 7 (OP-1)', Oral Surg Oral Med Oral Pathol Oral Radiol Endod (2010) 109(5): 531-540.

(Continued)

*Primary Examiner* — Elizabeth C Kemmerer
(74) *Attorney, Agent, or Firm* — Santosh K. Chari; Blake, Cassels & Graydon LLP (57) ABSTRACT

A system for multiphasic delivery of at least one growth factor at a treatment site comprises a delivery vehicle for releasing at least one growth factor in an initial release profile and a carrier for releasing at least one growth factor in a sustained release profile. The initial release profile releases at least one growth factor over a period of hours to days, wherein the growth factor is released in a large amount initially, with the remainder being released in progressively lower amounts. The sustained release profile releases at least one growth factor over a period of days to weeks, wherein the growth factor is released at a generally constant amount over such period. The system of the invention is particularly suited for applications on bioimplants. The invention also comprises methods and kits for multiphasic delivery of at least one growth factor.

21 Claims, 8 Drawing Sheets

(56) References Cited

U.S. PATENT DOCUMENTS

| | | |
|---|---|---|
| 2002/0015737 A1 | 2/2002 | Shih et al. |
| 2006/0257488 A1 | 11/2006 | Hubbard |
| 2006/0257492 A1* | 11/2006 | Wen .................. A61K 33/42 424/489 |
| 2007/0190102 A1 | 8/2007 | Luo |
| 2007/0248675 A1 | 10/2007 | Tae et al. |
| 2007/0255422 A1 | 11/2007 | Wei et al. |
| 2008/0233165 A1 | 9/2008 | Alexander et al. |
| 2010/0021518 A1 | 1/2010 | Scifert |
| 2011/0182911 A1 | 7/2011 | Clokie et al. |
| 2011/0208305 A1 | 8/2011 | Malinin et al. |

OTHER PUBLICATIONS

Boden, 'The ABCs of BMPs', Orthopaedic Nursing (2005) 24(1): 49-52.
Clokie et al., 'Recombinant Human Transforming Growth Factor β-1 and Its Effects on Osseointegration', Journal of Craniofacial Surgery (2003) 14(3): 268-277.
Clokie et al., 'Bone Morphogenetic Protein Excipients: Comparative Observations on Poloxamer', Plastic and Reconstructive Surgery (2000) 105(2): 628-637.
Fness et al., 'Characterization of absorbable collagen sponges as rhBMP-2 carriers', International Journal of Pharmaceutics (1999) 187: 91-99.
Hoffman et al., 'Perspectives in the biological function, the technical and therapeutic application of bone morphogenetic proteins', Appl Microbiol Biotechnol (2001) 57: 294-308.
Hollinger et al., 'Recombinant Human Platelet-Derived Growth Factor: Biology and Clinical Applications', J Bone Joint Surg Am. (2008) 90(1): 48-54.
Hu et al., 'The Osteoinductive Activity of Bone Morphogenetic Protein (BMP) Purified by Repealed Extracts of Bovine Bone', Growth Factors (2004) 22(1): 29-33.
Humber et al., 'Bone healing with an in situ-formed bioresorbable polyethylene glycol hudrogen membrane in rabbit calvarial defects', Oral Surg Oral Med Oral Pathol Oral Radiol Endod (2010) 103: 372-384.
Kawaguchi et al., 'Local Application of Recombinant Human Fibroblast Growth Factor-2 on Bone Repair: A Dose-Escalation Prospective Trial on Patients with Osteotomy', Journal of Orthopaedic Research (2007) 25: 480-487.
Kawai et al., 'Quantitative Computation of induced Heterotopic Bone Formation by an Image Analysis System', Clin. Orthop Relat. Res., (1988) 233:262-267.
Kirsch et al., 'BMP-2 antagonists emerge from alterations in the low-affinity binding epitope for receptor BMPR-II', The EMBO Journal (2000) 19(13): 3314-3324.
Peel et al., 'In Search of the Ideal Bone Morphogenetic Protein Delivery System In Vitro Studies on Demineralized Bone Matrix, Purified, and Recombinant Bone Morphogenetic Protein', Journal of Craniofacial Surgery (2003) 14(3): 284-291.
Rasubala et al., 'Platelet-derived growth factor and bone morphogenetic protein in the healing of mandibular fractures in rats', British Journal of Oral and Maxillofacial Surgery (2003)41 173-178.
Ruppert et al., 'Human bone morphogenetic protein 2 contains a hepann-binding site which modifies in biological activity', Eur. J. Biochem. (1996) 237:295-302.
Steinmuller-Nethl et al., 'Strong binding of bioactive BMP-2 to nanocrystalline diamond by physisorption', Biomaterials (2003) 27: 4547-4556.
Street et al., 'Vascular endothelial growth factor stimulates bone repair by promoting angiogenesis and bone turnover', PNAS (2002) 99(15) 9656-9661.
Tyndall et al., 'Decreased Platelet Derived Growth Factor Expression During Fracture Healing in Diabetic Animals', Clinical Orthopaedics and Related Research (2003) 408: 319-330.
Uludag et al., 'Characterization of rhBMP-2 pharmacokinetics implanted with biomaterial carriers in the rat ectopic model', J. Biomed. Mater. Res. (1999)46:193-202.
Vallejo et al., 'Renaturation and purification of bone morphogenetic protein-2 produced as inclusion bodies in high-cell-density cultures of recombinant *Escherichia coli*', Journal of Biotechnology (2002) 94: 185-194.
Wang et al., 'Recombinant human bone morphogenetic protein induces bone formation', Proc. Natl. Acad. Sci USA (1990) 87 2220-2224.
Winn et al., 'Sustained release emphasizing recombinant human bone morphogenetic protein-2', Advanced Drug Delivery Reviews (1998) 31: 303-318.
Yeh et al., 'Cartilage-Derived Morphogenetic Proteins Induce Osteogenic Gene Expression in the C2C12 Mesenchymal Cell Line', Journal of Cellular Biochemistry (2005) 95: 173-188.
International Search Report issued on PCT/CA2012/050234 on Aug. 8, 2012.
Chinese Search Report issued on Chinese Patent Application No. 201280017716.1 on Dec. 17, 2014.
Chen, F. et al., Journal of International Medicine: Stomatology, vol. 32, No. 1, pp. 44-46. Jan. 31, 2005.
Hu, Rongfeng, Industry Pharmaceutics, 1st Edition, p. 436, Aug. 31, 2010.
Search Report issued in Chinese patent application No. 201280017716.1 dated Nov. 4, 2015.
Aberg et al., Journal of Biomaterials Applications, vol. 26, Feb. 2012, p. 667-685.
Chen et al., J. Craniofacial Surg., 2010, 21:188-197.
Damien, C et al., J. Biomed. Mat. Res., 1990, 24: 639-654.
Damien, C et al.,Spine, 2002, 16S: S50-S58.
Gore, ed., Spectrophotometry and Spectrofluorimetry: A Practical Approach. Oxford University Press, 2000.
Gosling, ed., Immunoassays: A Practical Approach, Oxford University Press. 2000.
Harlow and Lane, Using Antibodies: A Laboratory Manual, Cold Spring Harbor Laboratory Press. 1999.
Hockfield et al., Selected Methods for Antibody and Nucleic Acid Probes. Cold Spring Harbor Laboratory Press. 1993.
Meyer et al. J Bone Jt. Surg 2003, 85-A: 1243-1254.
Millner, ed., High Resolution Chromatography: A Practical Approach. Oxford University Press, 1999.
Oliver, ed., HPLC of Macromolecules: A Practical Approach., Oxford University Press, 1998.
Szpalski et al., The Journal of Carniofacial Surgery, vol. Issue 23/3, May 2012, p. 638-644.
Zhou, et al. J. Craniofac Surg., 2007, 18(6), 1264-75.
International Search Report issued in PCT/CA2012/050738 (Oct. 17, 2013).
Search Report issued in Japanese patent application No. 2014-504131 dated Jan. 25, 2016.

\* cited by examiner

SYSTEM AND METHOD FOR MULTIPHASIC RELEASE OF GROWTH FACTORS

CROSS REFERENCE TO PRIOR APPLICATIONS

This application is a national stage application of PCT International Patent Application No. PCT/CA2012/050234, filed Apr. 11, 2012, which claims priority under the Paris Convention from U.S. Application No. 61/474,049, filed on Apr. 11, 2011, the entire contents of which are incorporated herein by reference.

FIELD OF THE INVENTION

This invention relates to systems and methods for releasing biological substances. In particular, the invention relates to the release of growth factors associated with bioimplants. More particularly, the invention provides a system and method for producing a multiphasic release profile of at least one growth factor to improve the performance of the bioimplant.

BACKGROUND OF THE INVENTION

Growth factors (GFs) are peptides and proteins that stimulate the growth and/or differentiation of cells via the interaction of the GFs with specific cell surface receptors. Growth factors play an integral role in the repair and regeneration of tissues and exogenous application of GFs can be used to stimulate the repair of various tissues and organs including bone, cartilage, skin and mucosa and to enhance repair of tissues through the stimulation of angiogenesis at the repair site.

The transforming growth factor beta (TGFβ) superfamily of secreted growth and differentiation factors in mammals has over 30 members. These dimeric proteins are characterized by a conserved seven cystine knot-based structure. They regulate the proliferation, differentiation and migration of many cell types, and have important roles in morphogenesis, organogenesis, tissue maintenance and wound healing. The TGFβ superfamily of growth factors can be subdivided into several subfamilies including the transforming growth factor beta subfamily, the bone morphogenetic protein (BMP) and growth and differentiation factor (GDF) family (also called the BMP subfamily), and the inhibin and activin subfamily.

The BMP subfamily of the TGFβ superfamily comprises at least twenty proteins, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15 (for a review, see e.g., Azari et al. Expert Opin Invest Drugs 2001; 10:1677-1686).

BMPs have been shown to stimulate matrix synthesis in chondroblasts; stimulate alkaline phosphatase activity and collagen synthesis in osteoblasts, induce the differentiation of early mesenchymal progenitors into osteogenic cells (osteoinduction), regulate chemotaxis of monocytes and mesenchymal cells, and regulate the differentiation of neural cells (for a review, see e.g., Azari et al. Expert Opin Invest Drugs 2001; 10:1677-1686 and Hoffman et al. Appl. Microbiol. Biotech 2001; 57:294-308).

One of the many functions of BMP proteins is to induce cartilage, bone, and connective tissue formation in vertebrates. The most osteoinductive members of the BMP subfamily are BMP-2, BMP-4, BMP-6, BMP-7, BMP-8 and BMP-9 (see, e.g., Hoffman et al., Appl. Microbiol Biotech 2001, 57-294-308; Yeh et al., J Cellular Biochem., 2005; 95-173-188; and Boden, Orthopaedic Nursing 2005, 24:49-52). This osteoinductive capacity of BMPs has long been considered very promising for a variety of therapeutic and clinical applications, including fracture repair; spine fusion; treatment of skeletal diseases, regeneration of skull, mandibular, and bone defects; and in oral and dental applications such as dentogenesis and cementogenesis during regeneration of periodontal wounds, extraction socket grafting, alveolar ridge augmentation, and sinus augmentation. Currently, recombinant human BMP-2 sold as INFUSE® by Medtronic FDA approved for use in spinal fusion surgery, for repair of fracture non-unions and for use in oral surgery, while and recombinant human BMP-7 sold as OP-1® by Stryker is approved as an alternative to autograft in recalcitrant long bone nonunion and for revision posterolateral (intertransverse) lumbar spine fusions, where autograft and bone marrow harvest are not feasible or are not expected to promote fusion Other recombinant growth factors that have been used exogenously to enhance bone repair include various TGFβs (see Clokie & Bell, J. Craniofacial Surg. 2003, 14:268-77), members of the fibroblast growth factor superfamily (FGFs) (see Kawaguchi et al., (2007) J. Orthopaedic Res. 25(4): 480-487), members of the platelet derived growth factor superfamily (PDGFs) (see Hollinger et al., 2008 JBJS 90(s1):48-54), and vascular endothelial growth factor (VEGF) (Street et al., 2002 PNAS 99:9656-61)

For these growth factors to be effective they must be active and available at a sufficient concentration at the time when critical densities of the appropriate responsive cells are present in the repair site. The short half-life, thermal instability, sensitivity to proteases and/or solubility of the GFs requires their administration in combination with a carrier to achieve this requirement.

A number of carriers have been evaluated for the delivery of GFs. These include fibrous collagen sponges, gelatin hydrogels, fibrin gels, heparin, reverse phase polymers such as the poloxamers, scaffolds composed of poly-lactic acid (PLA), poly-glycolic acid (PGA) or their co-polymers (PLGA), heparin-conjugated PLGA scaffolds, and inorganic materials such as calcium phosphates. For example the bioimplant (GEM-21S®) which is used for periodontal regeneration uses beta tricalcium phosphate (β-TCP) as the carrier for rhPDGF-BB.

However, these carriers are of limited effectiveness, due to loss of growth factor activity when associated with the carrier, inefficient release of the GF at the implantation site, and/or poor protection from proteolysis and degradation. For example the bioimplant Infuse® uses a type I collagen sponge as the carrier for rhBMP-2. The rhBMP-2 is released in a burst from the carrier and the half life of the BMP within the wound site is 1-3 days (Winn et al., 1998, Adv. Drug Del. Rev. 31:303; Friess et. al., 1999, Intl. J. Pharm., 187:91). By the time the mesenchymal stem cells which regenerate bone have migrated into the wound site only fractions of a percent of the original amount of BMP loaded is present to stimulate these cells to make bone. The current solution to ensure an effective level of BMP remaining at these later times is to significantly increase the amount of BMP that is initially loaded. These increased doses increase the risk of complications including bone formation beyond the implant site, autoimmune responses and potentially cancer. Further this dramatically increases the cost of the implant.

Therefore, a need exists in the art for materials and methods which release growth factors with a profile which minimizes the amount of growth factor that needs to be loaded to achieve the required therapeutic effect.

One strategy is to encapsulate the GF in a biodegradable polymeric matrix that releases the GF with a sustained release profile over many days. For example BMPs have been combined with poly-lactic acid (PLA) or poly-lactic co-glycolic acid (PLGA) to produce sustained release profiles. However the incorporation of the BMP in the PLA or PLGA can denature the BMP reducing its activity and it is difficult to manipulate the release profile to optimize the effectiveness of the bioimplant. Further the degradation rate of these carriers is typically such that large amounts of GF remain locked away long after healing is complete.

Another strategy is to chemically immobilize the GF directly onto the carrier retain it at the implant site. However this may also result in partial or complete loss of activity of the GF, and restricts the GF activity such that only those cells directly in contact with the carrier are able to interact with the GF and respond (see Steinmuller-Nethl, D. et al., Biomaterials, 2006, 27: 4547-56) which is not desirable as the effect is limited to the immediate interface with the carrier and not throughout the wound site.

In nature during wound healing multiple GF are present within the wound site and surrounding tissue at varying concentrations at different times. For example, immediately following bone fracture, platelets at the injury site will initially release large amounts of PDGF, with a sharp decline in protein levels within the fracture site over the following days (see Tyndall et al., Clinical Orthopaedics and Related Research, 2003, 408: 319-330). Conversely BMP-2 is expressed at all stages of the fracture healing process (see Rasubala et al. British Journal of Oral and Maxillofacial Surgery, 2003, 41: 173-178). The concentration of these growth factors is estimated to be orders of magnitude lower than those used during therapeutic application of exogenous GF due to matching of the concentration to the cellular requirements and synergistic effects of the multiple growth factors. Producing a system that allows the delivery of growth factors with multiphasic release profiles and the release of multiple growth factors with different release profiles would permit the use of bioimplants with GF release profiles that more closely mimic GF release during the natural healing process than current bioimplants that release a single growth factor in a burst or with sustained release.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention provides, in one aspect, a system, method and kit for the multiphasic release of at least one growth factor at, for example a treatment site. For this purpose, the system of the invention may be provided as a bioimplant or the like. In one aspect, the method of the invention delivers at least one growth factor in an initial release followed by the delivery of at least one growth factor in a "sustained release profile". The invention utilizes a delivery system for the initial release and a carrier for the sustained release.

In one aspect, the same growth factor is released in the initial and sustained release profiles. In another aspect, different growth factors are released, with a first growth factor released in an initial profile and a second growth factor released in a sustained release profile. As will be known to persons skilled in the art, the release of two different growth factors in such differing manners is believed to more closely mimic the natural growth factor release system at a treatment site.

In accordance with one aspect of the invention, there is provided a carrier that provides a sustained release of at least one growth factor, combined with a delivery vehicle that provides an initial release of at least one growth factor. The combination of the carrier and the delivery vehicle results in a multiphasic release profile of the growth factor(s).

In preferred embodiments the growth factor ("GF") is a member of the transforming growth factor beta (TGFβ) superfamily. In particularly preferred embodiments the growth factor is a bone morphogenetic protein (BMP).

In one aspect of the present invention, the carrier ("CAR") is formed of calcium phosphate particles dispersed within a polymer scaffold or matrix. In one aspect, the scaffold or matrix is further coated with a hydroxyapatite layer.

In one embodiment the at least one growth factor is/are applied as a liquid to the calcium particles and are then lyophilized onto the particles before combining with the polymer matrix.

In another aspect of the present invention the carrier is formed by mixing one or more calcium phosphate powders with a liquid solution containing at least one growth factor to produce a calcium phosphate cement. In one aspect, the cement is then ground into particles.

In preferred embodiments the delivery vehicle is a reverse phase polymer. In particularly preferred embodiments the reverse phase polymer is a poloxamer, more particularly poloxamer 407 (also called Pluronic™ F127).

As indicated above, in one aspect, the carrier and the delivery vehicle are adapted to release the same growth factor while in another aspect, the carrier and delivery vehicle are adapted to release different growth factors. In yet another aspect of the invention, the carrier and delivery vehicle are each adapted to release combinations of two or more growth factors, with the combination released by each being the same or different.

Thus, in one aspect, the invention provides a system for multiphasic release of growth factors at a treatment site, the system comprising:

a delivery vehicle comprising at least one first growth factor; and
a carrier comprising at least one second growth factor;
wherein:
the delivery vehicle is adapted to release the at least one first growth factor in an initial release profile over a first time period;
the carrier is adapted to release the at least one second growth factor in a sustained release profile over a second time period.

In another aspect, the invention provides a method of multiphasic release of growth factors, the method comprising:

delivering at least one first growth factor with an initial release profile;
delivering at least one second growth factor in a sustained release profile.

In a further aspect, the invention provides a kit for multiphasic delivery of growth factors, the kit comprising:
a delivery vehicle component;
at least one first growth factor associated with the delivery vehicle;
a carrier component; and
at least one second growth factor associated with the carrier.

BRIEF DESCRIPTION OF THE DRAWINGS

The invention will now be described with reference to the appended figures, which are briefly described below.

DETAILED DESCRIPTION OF THE INVENTION

Growth factors (GF) play an integral role in the repair and regeneration of tissues and exogenous GFs can be used to stimulate the repair of various tissues and organs. For exogenous growth factors to be effective in stimulating repair they must be retained at the site requiring repair, and be protected from inactivation, sequestration or degradation. To achieve this carriers are used. However the release of growth factors from these carriers is not ideal and cannot be easily modified. The current invention is based on the discovery that the multiphasic release of growth factors from a bioimplant increases the efficacy of the implant.

The present inventors have developed methods and materials for enhancing the efficacy of, for example, bioimplants by improving the release kinetics or release profile of growth factors at sites of implantation, while maintaining the activity of the growth factors. In one aspect, the present invention provides a growth factor delivery system and method comprising a carrier containing at least one growth factor, combined with a delivery vehicle also containing at least one growth factor. The at least one growth factor released by the carrier and delivery vehicle may be the same or different.

The system and method of the invention can be used for a variety of therapeutic and clinical applications, including: fracture repair; bone grafts; spine fusion; and regeneration of skull, mandibular, and bone defects. For such applications, the system of the invention is preferably provided on, or in the form of a bioimplant.

Definitions

Unless defined otherwise below, all technical and scientific terms used herein have the same meaning as commonly understood by one of ordinary skill in the art to which this invention belongs.

As used herein the term "bioimplant" refers to a material which is suitable for implantation and contains an exogenous growth or biologically active factor. As discussed further herein, the system of the present invention is preferably used by applying same to a bioimplant. The bioimplant is then provided within a body of a subject wherein the system releases at least one growth factor in a multiphasic release profile.

As used herein the term "growth factor" refers to peptides and proteins that stimulate the growth and/or differentiation of cells via the interaction of the GFs with specific cell surface receptors. Examples of growth factors include the bone morphogenetic proteins (BMPs), transforming growth factor beta (TGFβ), the insulin-like growth factors (IGF), the fibroblast growth factors (FGFs), platelet derived growth factor (PDGF) and vascular endothelial growth factor. In preferred embodiments the growth factors are BMPs.

By "recombinant" is meant a protein produced by a transiently transfected, stably transfected, or transgenic host cell or animal as directed by an expression construct containing the cDNA for that protein. The term "recombinant" also encompasses pharmaceutically acceptable salts of such a polypeptide As used herein, the term "polypeptide" or "protein" refers to a polymer of amino acid monomers that are alpha amino acids joined together through amide bonds. Polypeptides are therefore at least two amino acid residues in length, and are usually longer. Generally, the term "peptide" refers to a polypeptide that is only a few amino acid residues in length. A polypeptide, in contrast with a peptide, may comprise any number of amino acid residues. Hence, the term polypeptide included peptides as well as longer sequences of amino acids.

As used herein, the terms "bone morphogenetic protein" or "bone morphogenic protein" or "BMP" are used interchangeably and refer to any member of the bone morphogenetic protein (BMP) subfamily of the transforming growth factor beta (TGFβ) superfamily of growth and differentiation factors, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15.

The terms "bone morphogenetic protein" and "BMP" also encompass allelic variants of BMPs, function conservative variants of BMPs, and mutant BMPs that retain BMP activity. The BMP activity of such variants and mutants may be confirmed by any of the methods well known in the art (see the section Assays to measure BMP activity, below) or as described in Example 1

In preferred embodiments, the BMP is BMP-2, BMP-4, BMP-5, BMP-6, BMP-7, BMP-8 or BMP-9. In particularly preferred embodiments the BMP is BMP-2, BMP-4 or BMP-7.

In preferred embodiments the BMP is a mammalian BMP (e.g., mammalian BMP-2 or mammalian BMP-7). In particularly preferred embodiments, the BMP is a human BMP (hBMP) (e.g. hBMP-2 or hBMP-7).

As used herein the term "scaffold" refers to a material whose purpose is to provide a structure which supports cell adhesion, migration and ingrowth into a tissue repair site.

As used herein the term "carrier" refers to a material comprising single or multiple components and is adapted to release at least one growth factor at a treatment site in a "sustained release" profile over a period of time. In one aspect, the period of time taken by the carrier to release the at least one growth factor is between several days and several weeks. Preferably, the carrier is adapted to release the at least one growth factor over a period of weeks.

In preferred embodiments the carrier also acts as a scaffold or matrix. As discussed above, in one aspect of the invention, the carrier is formed of calcium phosphate particles dispersed within a macroporous polymer scaffold or matrix. In one aspect, the scaffold or matrix is further coated with a hydroxyapatite layer. In one embodiment the at least one growth factor is applied as a liquid to the calcium particles and are then lyophilized onto the particles before combining with the polymer matrix.

As used herein the term "delivery vehicle" refers to a material which comprises or contains at least one growth factor and is adapted to release the at least one growth factor at a treatment site in an initial release profile over a time period. In one aspect, the material forming the delivery vehicle is in the form of a gel. In one aspect, the period of time taken by the delivery vehicle to release the at least one growth factor is between several hours and several days. In a preferred embodiment of the invention, the delivery vehicle releases the majority of the at least one growth factor in an "initial release" or "initial release profile" that lasts a period of hours. Preferably, the delivery vehicle is adapted to release at least 80% of the growth factor(s) contained therein (or associated therewith) within a period of 72 hours.

In preferred embodiments the delivery vehicle is a reverse phase polymer. As used herein the term "reverse phase" refers to the property whereby the polymer undergoes a reversible temperature dependent transition from a liquid to a gel. In one aspect the transition temperature is between 15° C. and 37° C. Preferably the transition temperature is between 15° C. and 25° C. As would be known to persons skilled in the art, "normal phase" materials increase their viscosity with a decline in temperature. In contrast, reverse phase materials show a decline in viscosity as the temperature drops below their transition temperature.

In particularly preferred embodiments the reverse phase polymer is a poloxamer, more particularly Pluronic™ F127 (also known as poloxamer 407).

As used herein the term "sustained release" or "sustained release profile" refers to the release of at least one growth factor, by the carrier, over a period of several days or weeks with the amount released over an initial period being similar to or less than the amount released over the same period after several days or weeks of implantation. Preferably, a sustained release profile lasts at least one week. As will be understood by persons skilled in the art, typically, the amount of growth factor released in a sustained release profile over the first three days will be less than the amount released over the following seven days.

Figure 2:
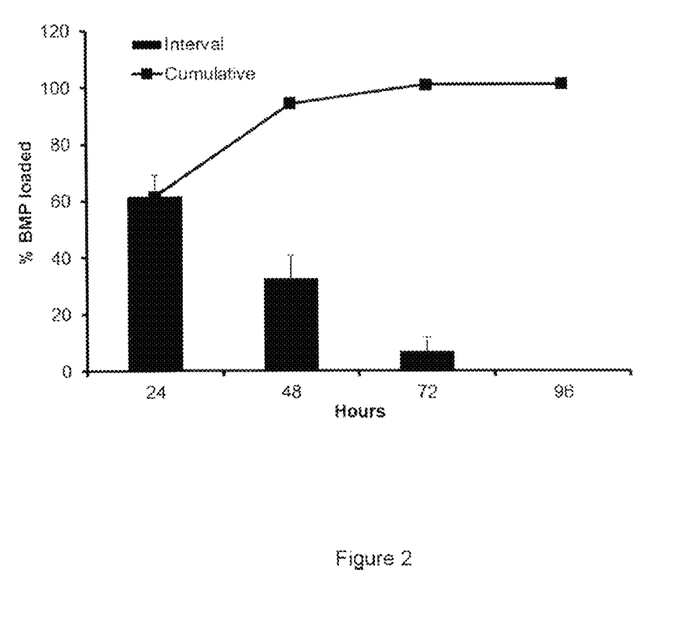
FIG. 2 illustrates the initial release profile exhibited by the delivery vehicle of the invention.

As used herein the term "initial release" or "initial release profile" refers to the initial release, by the delivery vehicle, of a large amount of at least one growth factor followed by progressively smaller amounts released over a period of hours or days. In one aspect, an initial release profile results in the delivery of at least 80% of the loaded growth factor(s) within a period of roughly 72 hours. An initial release profile is illustrated in FIG. 2.

As used herein the term "multiphasic release" refers to an initial release of the at least one growth factor over an initial period of time, followed by "sustained" release of the at least one growth factor over a second period of time. Preferably, the initial period of time is roughly several hours and the second period of time is roughly several days to weeks. Such a release profile may also be referred to as "biphasic release" since it occurs in two stages. In preferred embodiments, the initial release is provided by the delivery system of the invention and the "sustained" release is provided by the carrier of the invention.

In one aspect of the invention, the delivery vehicle component comprises at least 10% and not more than 50% of the total amount of growth factor(s) delivered by the system of the invention and the carrier component comprises at least 50% of the total amount of growth factor(s) delivered by the system.

Assays to Measure BMP Activity

Assays to characterize in vitro and in vivo function of recombinant BMPs are well known in the art, (see, e.g., U.S. Pat. No. 4,761,471; U.S. Pat. No. 4,789,732; U.S. Pat. No. 4,795,804; U.S. Pat. No. 4,877,864; U.S. Pat. No. 5,013,649; U.S. Pat. No. 5,166,058; U.S. Pat. No. 5,618,924; U.S. Pat. No. 5,631,142; U.S. Pat. No. 6,150,328; U.S. Pat. No. 6,593,109; Clokie and Urist, Plast. Reconstr. Surg. 2000; 105:628-637; Kirsch et al., EMBO J 2000; 19:3314-3324; Vallejo et al., J. Biotech. 2002; 94:185-194; Peel et al., J. Craniofacial. Surg. 2003; 14:284-291; and Hu et al., Growth Factors, 2004; 22:29-33).

Such assays include: in vivo assays to quantify osteoinductive activity of a BMP following implantation (e.g., into hindquarter muscle or thoracic area) into a rodent (e.g. a rat or a mouse) (see, for example, U.S. Pat. No. 4,761,471; U.S. Pat. No. 4,789,732; U.S. Pat. No. 4,795,804; U.S. Pat. No. 4,877,864; U.S. Pat. No. 5,013,649; U.S. Pat. No. 5,166,058; U.S. Pat. No. 5,618,924; U.S. Pat. No. 5,631,142; U.S. Pat. No. 6,150,328; U.S. Pat. No. 6,503,109; Kawai and Urist., Clin. Orthop. Relat. Res., 1988; 222:262-267; Clokie and Urist, Plast. Reconstr. Surg., 2000; 105:628-637; and Hu et al., Growth Factors, 2004; 22:29-33); in vivo assays to quantify activity of a BMP to regenerate skull trephine defects in mammals (e.g., rats, dogs, or monkeys) (see, for example, U.S. Pat. No. 4,761,471 and U.S. Pat. No. 4,789,732); in vitro assays to quantify activity of a BMP to induce proliferation of in vitro cultured cartilage cells (see, for example, U.S. Pat. No. 4,795,804); in vitro assays to quantify activity of a BMP to induce alkaline phosphatase activity in in vitro cultured muscle cells (e.g., C2C12 cells, ATCC Number CRL-1772) or bone marrow stromal cells (e.g., murine W-20 cells, ATCC Number CRL-2623) (see, for example, U.S. Pat. No. 6,593,109; Ruppert et al., Eur J Biochem 1996; 237:295-302; Kirsch et al., EMBO J, 2000; 19:3314-3324; Vallejo et al., J Biotech, 2002; 94:185-194; Peel et al., J Craniofacial Surg., 2003; 14:284-291; and Hu et al., Growth Factors, 2004; 22:29-33); in vitro assays to quantify activity of a BMP to induce FGF-receptor 2 (FGFR3) expression in cultured mesenchymal progenitor cell lines (e.g., murine C3H10T1-2 cells) (see, for example, Vallejo et al. J Biotech 2002; 94:185-194); in vitro assays to quantify activity of a BMP to induce proteoglycan synthesis in chicken limb bud cells (see, for example, Ruppert et al., Eur J Biochem 1996; 237:295-302); and in vitro assays to quantify activity of a BMP to induce osteocalcin treatment in bone marrow stromal cells (e.g., murine W-20 cells; ATCC Number CRL-2623) (see, for example, U.S. Pat. No. 6,593,109).

Assays to Measure BMP Binding and Release

Various assays can be used to measure binding and release of recombinant BMP from a carrier. For example, the amount of recombinant BMP protein can be quantified by any of the techniques well known in the art, including dot blots, immunoassay (e.g., enzyme linked immunosorbent assays, ELISA), measurement of the increase in radioactivity present in the release buffer when the bioimplant incorporates radiolabeled BMP and chromatography (e.g., high pressure liquid chromatography, HPLC and ion-exchange chromatography).

Such methods are well known in the art (See for example, Harlow and Lane, Using Antibodies: A Laboratory Manual, Cold Spring Harbor Laboratory Press. 1999; Gosling, ed., Immunoassays: A Practical Approach, Oxford University Press. 2000; Oliver, ed., HPLC of Macromolecules: A Practical Approach., Oxford University Press, 1998; Millner, ed., High Resolution Chromatography: A Practical Approach. Oxford University Press, 1999; Hockfield et al., Selected Methods for Antibody and Nucleic Acid Probes. Cold Spring Harbor Laboratory Press. 1993; Gore, ed., Spectrophotometry and Spectrofluorimetry: A Practical Approach. Oxford University Press, 2000).

For example, protocols for radioimmunoassay analysis of BMP proteins have been described (see, for example, U.S. Pat. No. 4,857,456). For example, protocols for immunoblot analysis of BMP proteins have been described (see, for example, Wang et al. Proc Natl Aced Sci USA 1990; 87:2220-2224). For example, ELISA kits for the quantitation of protein levels of human, rat, or mouse BMP-2 are commercially available, for example, from R&D Systems (catalog #DBP200, PDBP200, or SBP200). For example, ELISA kits for the quantitation of protein levels of human BMP-7 are commercially available, for example, from R&D Systems (catalog #DY354 or DY354E).

Kits

In one aspect, the invention provides a kit for containing the system described herein. In one embodiment, the kit comprises the necessary components for making the delivery vehicle and the carrier as well as the needed growth factors. That is, the kit of the invention would comprise the necessary components for making the delivery vehicle and the carrier as well as least one growth factor associated with the delivery vehicle and at least one growth factor associated with the carrier.

Preferably, the delivery vehicle and the associated growth factor(s) are maintained in separate containers, to be combined at the time of use. This would be particularly preferable in cases where the delivery vehicle may comprise a liquid or a gel. In such case, the associated growth factor(s) may be kept in a separate container as a lyophilized powder. At the time of use, the growth factor(s), in powder form, may be combined with the liquid or gel delivery vehicle.

The kit preferably comprises a further container comprising the carrier onto which may be loaded or coated the associated growth factor(s). In one embodiment, the carrier material may also be maintained separate from the associated growth factor(s).

In a preferred embodiment, the kit of the invention would comprise at least three containers for each of the following: 1) the delivery vehicle component; 2) the at least one first growth factor (i.e. the growth factor(s) associated with the delivery vehicle); and, 3) the carrier and the least one second growth factor (i.e. the growth factor(s) associated with the carrier). In use, the at least one second growth factor, in powder form, is combined with the liquid or gel form delivery vehicle and the mixture is then applied to the carrier onto which the at least one second growth factor was pre-loaded.

In one aspect, the kit of the invention may comprise any necessary reagents and/or instructions and/or vessels as may be needed.

EXAMPLES

The present invention will now be described by means of the following examples. These examples illustrate the novel findings by the inventors that a multiphasic release profile of a growth factor, such as rhBMP-2 produced by loading part of the BMP within a carrier that releases BMP with a sustained release and part of the BMP within a delivery vehicle that releases BMP with an initial release is more effective than carriers that only produce a burst release or a sustained release.

As will be obvious to one skilled in the art it is possible to place one growth factor within the carrier and a different growth factor within the delivery vehicle, resulting in different release profiles of each growth factor.

It will be understood that the examples provided herein are intended solely to illustrate the present invention and not to limit the scope of the invention in any way. Likewise, the invention is not limited to any particular preferred embodiments described herein. Indeed, many modifications and variations of the invention may be apparent to those skilled in the art upon reading the present specification. The invention is therefore to be limited only by the terms of the appended claims, along with the full scope of equivalents to which the claims are entitled.

Example 1: Manufacture of a Sustained Release Composite Carrier Containing BMP by Encapsulation in PLGA This example demonstrates how to form a carrier containing rhBMP-2 and which releases the growth factor in a sustained release profile.

Materials and Methods

PLGA 75/25 with inherent viscosity of 1.33 dL/g (MW=205,000-210,000) was purchased from Birmingham Polymers Inc. (Birmingham, Ala.). Tetracalcium phosphate (TTCP) was obtained from Taihei Chemical Industrial Co. (Osaka, Japan) and dicalcium phosphate anhydrous (DCPA) and dimethyl sulfoxide (DMSO) were obtained from Sigma Chemical Co. (MO, USA). Sugar particles were purchased from Tate & Lyle North America Inc. (Toronto, Canada).

Resorbable calcium phosphate particles were prepared by mixing equimolar TTCP and DCPA with deionized distilled water (ddH2O) at 100% relative humidity for 24 h. The reactant was ground and sieved through 45 μm sieve.

Recombinant human BMP-2 (rhBMP-2, Induce Biologics Inc) in was prepared in formulation buffer (1.5 mg/ml, pH 4.5; 5 mm glutamic acid, 2.5% glycine, 0.5% sucrose and 0.01% Tween™ 80 with ddH$_2$O). The protein solution was added to vials containing CaP powder and agitated for at least 15 minutes. The powder was then frozen and lyophilized.

Particles with (CaP-BMP) or without (CaP) BMP were then used to make CaP particulate-PLGA scaffold blocks by phase-inversion/particle leaching as follows: PLGA was dissolved in DMSO at a concentration of 11.5% (w/v). To this solution, the CaP and CaP-BMP particles were thoroughly mixed according to a CaP/PLGA ratio of 2:1 (w/w). Sugar crystals with size ranges of 0.85-1.18 mm were dispersed in the CaP/PLGA and the mixture was solidified at −18° C. in a mold. The PLGA was precipitated and the sugar crystals leached out by soaking in three changes of $ddH_2O$.

A layer of hydroxyapatite was deposited onto and throughout the macroporous composite scaffolds as follows: dry PLGA/CaP cylinders, measuring 2 mm in diameter and 2 mm in length, were pre-wetted in 70% ethanol and immersed in 60 ml of 3×SBF for a period of 9 days at 37° C. SBF was prepared as follows: to 1.8 L of ddH2O under vigorous stirring the following salts were added sequentially 29.711 g NaCl, 2.206 g $CaCl_2$-$2H_2O$, 10 ml 1M HCl, 0.852 $Na_2HPO_4$. The final volume was brought to 2 L. The SBF solution was changed daily. Following coating, the 3PCC samples were rinsed in $ddH_2O$ and air dried.

Figure 1:
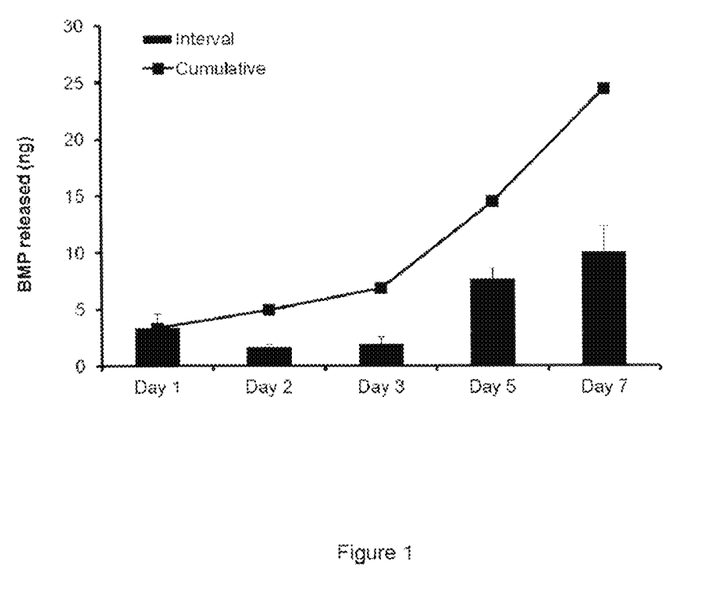
FIG. 1 illustrates a sustained release profile exhibited by the carrier of the invention.

This resulted in the formation of a macroporous composite carrier (3PS) that is able to release rhBMP-2 with a sustained release profile over at least seven days. These results are illustrated in FIG. 1.

Example 2: Manufacture of a Sustained Release Carrier Containing BMP by Encapsulation in a Calcium Phosphate Cement The present example demonstrates how to form a calcium phosphate cement (CPC) carrier containing rhBMP-2 that has a sustained release profile.

Materials and Methods

Tetracalcium phosphate (TTCP) was obtained from Taihei Chemical Industrial Co. (Osaka, Japan) and dicalcium phosphate anhydrous (DCPA) was obtained from Sigma Chemical Co. Macroporous biphasic calcium phosphate granules (Eclipse) were purchased from Citagenix (Laval Qc, Canada). Recombinant human BMP-2 (rhBMP-2, Induce Biologics Inc) was prepared in formulation buffer (1.5 mg/ml, pH 4.5; 5 mm glutamic acid, 2.5% glycine, 0.5% sucrose and 0.01% Tween™ 80 with ddH2O).

Resorbable calcium phosphate cement particles were prepared by mixing equimolar TTCP and DCPA with rhBMP-2 solution. The reactant was ground and sieved through a 300 and 100 μm sieve and particles between 100 and 300 μm, retained.

This resulted in the formation of calcium phosphate cement carrier particles into which the rhBMP-2 was incorporated. Upon implantation into an animal BMP is released in a sustained manner over a period of at least several weeks.

To produce a CPC based sustained release carrier that also acted as a macroporous scaffold CPC particles (0.1 to 0.3 mm) were mixed macroporous calcium phosphate granules (1-2 mm) in a 1:1 ratio (w/w).

Example 3: Manufacture of a Sustained Release Carrier Containing BMP by Use of a Coating that Binds BMP The present example demonstrates how to form a carrier that has a sustained release profile by applying a BMP binding coating. One such method is to coat a scaffold with an antibody or BMP binding protein as described in our co-pending application number U.S. application Ser. No. 13/002,444 (the entire content of which is incorporated herein by reference).

Materials and Methods

Purified polyclonal rabbit anti-human BMP-2 antibodies were purchased from Cell Sciences, (Canton Mass., Cat #PA0025). Macroporous biphasic calcium phosphate (BCP) granules (Eclipse) were purchased from Citagenix (Laval, Qc, Canada.)

Sterile BCP granules were weighed out in a biosafety cabinet and placed in sterile TPP tubes (Mandel Scientific, Guelph ON, Canada). The antibody solution was diluted in phosphate buffered saline to final concentration of 150, 300 and 600 ng of antibody in 1 ml PBS, filter sterilized and applied to the scaffold at a 1:1 v/v ratio. The samples were agitated for at least 15 minutes at room temperature, before being frozen and lyophilized. BMP solution was then applied to the granules, allowed to soak for 15 minutes at room temperature and then frozen and re-lyophilized.

This resulted in the formation of a BCP granules coated with antibody that bound and slowly released the rhBMP-2 in a sustained fashion.

The amount of rhBMP-2 that can be bound can be increased by increasing the amount of antibody used. The rate of release can be increased by using antibodies with lower affinity or avidity.

Example 4: Production of a BMP Containing Delivery Vehicle Using F127

The present example demonstrates how to prepare a delivery vehicle containing rhBMP-2 using F127.

Materials and Methods

Poloxamer was prepared as follows: 100 ml of distilled water was chilled to 4° C. and various amounts of poloxamer 407 were added slowly with stirring over a period of several hours, until all the solid prill was dissolved making a final solution ranging between 12 and 33%. The poloxamer solution was then sterilized in an autoclave (121° C., 20 minutes, 30 psi). Following sterilization, the poloxamer solution was kept at 4° C. until use.

Lyophilized recombinant human BMP-2 powder (rhBMP-2, Induce Biologics Inc) was added to the poloxamer solution and was slowly mixed.

Alternatively rhBMP-2 was added from solution (1 mg/ml, pH 4.5; 5 mm glutamic acid, 2.5% glycine, 0.5% sucrose and 0.01% Tween 80) at a 1/10 or 1/20 ratio (v/v).

This resulted in the formation of a delivery vehicle that released more than 80% of the rhBMP-2 over the first two days (as illustrated in FIG. 2).

Example 5: Production of a Bioimplant with a Multiphasic Release Profile

The present example demonstrates how to form a 3PS-F127 bioimplant containing rhBMP-2 that releases the rhBMP-2 with a multiphasic release profile.

Materials and Methods

The 3PS carrier (as described in Example 1) containing 0, 4.55 or 9.1 μg of rhBMP-2 per 5 mg of carrier was prepared and stored in Eppendorf tubes. A delivery vehicle containing 0, 4.55 or 9.1 μg of rhBMP-2 in 45.5 μl F127 (prepared as described in Example 4) was stored in Eppendorf tubes at 4° C. Immediately prior to use, the F127 was pipetted onto the 3PS carrier and the carrier was mixed into the delivery vehicle.

This 3PS-F127 bioimplant was then used to measure BMP release in vitro and bone formation activity in vivo as described below.

The ratios of carrier to delivery vehicle can be varied to produce gel (1:1 ratio v:v) or putties (2:1 ratio v:v). Further the ratio of BMP to carrier or the particle size of the carrier can be varied to alter the sustained release profile. Finally the amount of rhBMP-2 in the carrier and the delivery vehicle can be varied to alter the amount of rhBMP-2 released initially over the first few hours compared to amount released over the following weeks.

Example 6: An In Vitro Assay for Release of BMPs from Bioimplants

The present example describes how to measure the release of rhBMP-2 from the various bioimplants described in Examples 1 to 5.

Materials & Methods

Bioimplants containing known amounts of rhBMP-2 prepared as in Examples 1 to 5 were transferred to Eppendorf tubes. The total amount of rhBMP-2 used was 9.1 µg of rhBMP-2 per 5 mg of carrier and 45.5 µl of F127, or 20 µg of rhBMP-2 to 10 mg of carrier to 100 µl of F127.

Samples were then incubated under agitation with a 1 ml solution of release buffer comprising phosphate buffered saline (PBS)+1% BSA at 37° C. The buffer was removed and replaced with fresh release buffer after various times (e.g. 1, 2, 5, 7 and 10 days) and the collected solutions were stored with 1.5 ml vials at −20° C. for further analysis.

The amount of BMP-2 released into the buffer was measured using a commercial ELISA (Quantikine™ hBMP-2 ELISA, RnD Systems). The ELISA was carried out according to the manufacturer's instructions.

Results

No BMP was detectable in release buffer collected from any of the bioimplants which had not been loaded with BMP. The carrier samples which had been loaded with rhBMP-2 demonstrated a sustained release of rhBMP-2 over the period of the study, while samples in the delivery vehicle alone were released in an "initial release profile".

When the carrier and delivery vehicle were combined, various release profiles were obtained depending on which component the BMP was loaded into. When 100% of the rhBMP-2 (9.1 µg) was loaded within the 3PS (5 mg) carrier which was then mixed with 33% F127 (45.5 µl), the BMP release profile matched the sustained pattern, where the amount of BMP released over the first 2 days was 5 ng, between days 3 and 5 it was 8 ng and between days 5 and 7 it was 10 ng (FIG. 3; 100-0).

Figure 3:
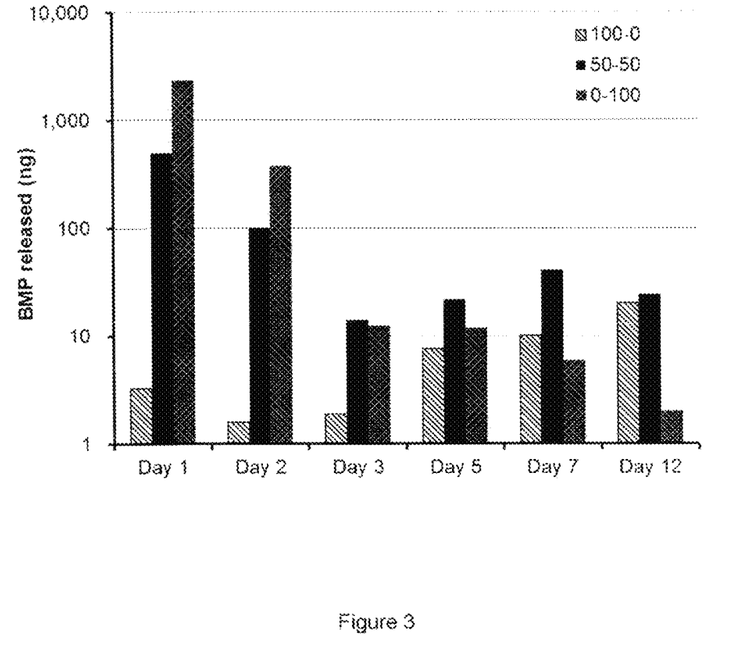
FIG. 3 illustrates differing release profiles based on an amount of growth factor in the delivery vehicle and carrier. A multiphasic release profile is observed when growth factors are incorporated into both the delivery vehicle and carrier (50-50).

When 100% of the rhBMP-2 (9.1 µg) was loaded within 33% F127 (45.5 µl) and then was then mixed with the 3PS carrier (5 mg) which had no BMP within it, the BMP was released where the amount of BMP released over the first 1 day was 2363 ng, over the second day was 381 ng and then 12 ng on the third day (FIG. 3; 0-100).

When the BMP was distributed between the carrier and the delivery vehicle the bioimplant demonstrated a biphasic release profile, with an intermediate initial release followed by sustained release of BMP (FIG. 3; 50-50).

Example 7: An In Vitro Assay to Test the Activity of Released BMPs

The present example describes how to determine whether the rhBMP-2 released from the bioimplants retains its activity. To demonstrate that the released rhBMP is biologically active, responsive cells can be cultured in with the releasate and their response to the growth factor measured. Such assays are known in the art (see Peel et al., J. Craniofac. Surg. 2003, 14:284-291).

Materials & Methods

Materials with or without rhBMP-2 as described in Examples 1 to 5 were prepared. Releasates were prepared as described in Example 3 except the buffer was alpha minimal essential medium with 15% fetal bovine serum and antibiotics (aMEM+15% FBS+AB)

C2C12 cells were seeded into 24 well tissue culture plates at $0.5 \times 10^5$ cells/ml, 1 ml alpha MEM+15% FBS per well. After various periods between 24 and 72 hours the media was removed and the various releasates were applied. Negative controls included C2C12 cells cultured with fresh aMEM+15% FBS+AB. Positive controls included C2C12 cells incubated with aMEM+15% FBS+AB containing 25, 50 and 100 ng/ml rhBMP-2. After 48 hours the cells were lysed in 1 ml cell lysis buffer (Cellytic Sigma Aldrich) and the alkaline phosphatase (ALP) activity of the cell lysates measured using the para-nitrophenol phosphate assay (Sigma Aldrich). The cell protein content of the lysates was measured using Coomassie Plus Reagent (Fisher) and was used to normalize ALP activity to the number of cells in each well.

Generally, to determine whether there has been any loss in activity of the BMP when associated with the carrier or delivery vehicle, a standard activity curve of ALP/PTN results for rhBMP-2 standards which have not been associated with the carrier or delivery vehicle is determined. The concentration of active rhBMP-2 in the releasates can be determined from this standard curve and this is expressed as a percentage of the total the amount of rhBMP-2 present in the releasates as determined by ELISA.

Example 8: Evaluation of Osteoinductive Activity of Multiphasic BMP Implants The present example describes how to determine the osteoinductive activity of BMP containing bioimplants in vivo. To evaluate the ability of bioimplants to induce bone formation the mouse muscle pouch assay was used. In this model the bioimplant is placed in a muscle pouch made in the hind limbs of the mouse and the size of the induced bone formed is proportional to the amount of BMP tested. Such assays are known in the art (see for example Barr et al., Oral Surg. Oral Med. Oral Pathol. Oral Radiol. Endod., 2010; 109:531-40.)

Materials and Methods

Bioimplants were prepared as described in Examples 1 and 5. Under anesthesia bilateral pouches were made in the thigh muscles of the hind limbs of male CD-1 mice aged 37-42 days, by blunt dissection. The bioimplants were then placed into sterile gelatin capsules which had been placed into the muscle pouch. The muscle was pulled together and the skin closed with Mitchel clips.

The animals were euthanized on post-op day 28. The hind limbs were harvested and fixed with 10% buffered formalin. Following fixation, the specimens were imaged using a microCT scanner (General Electric Healthcare eXplore™ Locus SP). Samples were scanned and reconstructed using the manufactures software at a resolution of 59 µm. Following image reconstruction, a region of interest (ROI) was determined. This area encompassed all areas containing the bioimplant induced bone. These can be easily distinguished from the skeletal bones based on location and density.

In order to analyze the quantity and quality of bone within the ROI, the voxels of the mCT images were segmented into bone and non-bone phases. Segmentation was achieved by determining a threshold value for the voxel grayscale at which the voxel was counted as bone. The total volume (TV), bone volume (BV), mineral density of the total volume (TV-MD), mineral density of the bone volume (BV-MD), mineral content of the total volume (TV-MC), mineral content of the bone volume (BV-MC) and bone volume fraction (BVF) of the ROI were determined for each sample. Values were adjusted for the presence of calcium due to the carrier by using an upper threshold value that selected only carrier and subtracting it from the values obtained using a lower threshold which included carrier plus new bone (see Humber et al., Oral Surgery, Oral Medicine, Oral Pathology, Oral Radiology, and Endodontology. 2010. 109:372-384).

Following completion of the microCT analysis, the specimens were either embedded in spurs resin or decalcified in formic acid and embedded in wax. Resin embedded samples were evaluated by backscatter SEM while wax embedded samples were cut and stained with hematoxylin and eosin (H&E) and examined by light microscopy to evaluate the tissue types present at the implantation site.

Results

A carrier and a delivery vehicle were combined as described in Example 5.

Figure 4:
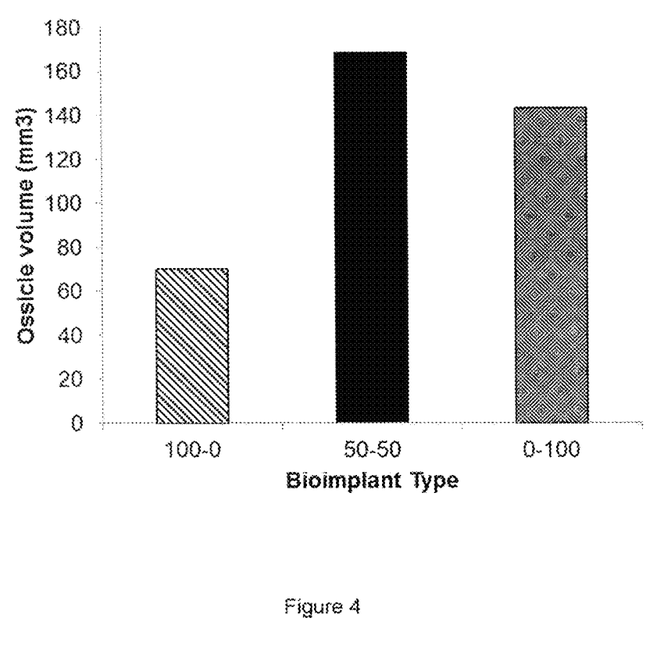
FIG. 4 illustrates the in vivo activity of the bioimplants where a growth factor is released as shown in FIG. 3 according to the method of the invention.

MicroCT analysis showed that bioimplants with all of the BMP within the 3PS carrier, which had a sustained BMP release profile, produced the smallest ossicles of bone (FIG. 4; 100-0), bioimplants with all of the BMP within the F127 delivery vehicle, which had a burst BMP release profile produced intermediate sized ossicles (FIG. 4; 0-100), while bioimplants with 50% of the BMP loaded into the carrier and 50% loaded into the delivery vehicle, which had a multi-phasic BMP release profile, produced the largest ossicles of bone (FIG. 4; 50-50).

Figure 5:
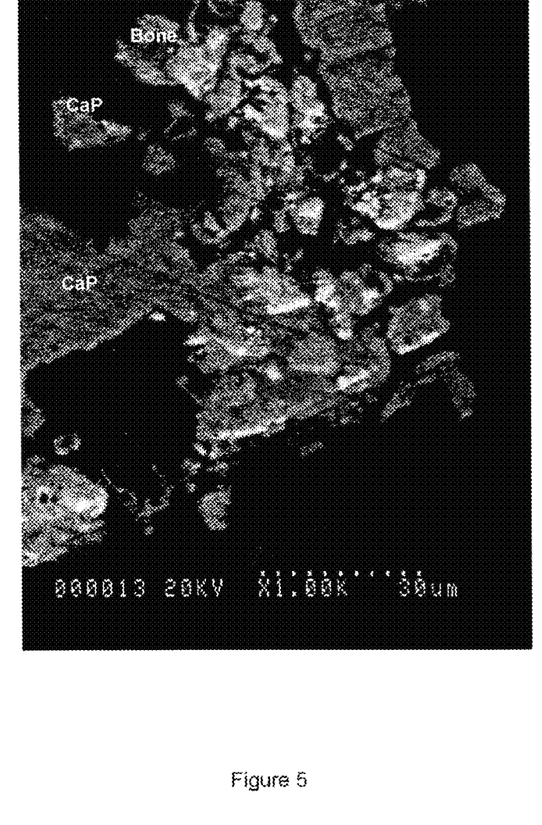
FIG. 5 illustrates the formation of new bone (Bone) onto calcium phosphate particles (CaP) when a bioimplant produced according to the method of the invention was implanted into a mouse.
Figure 6:
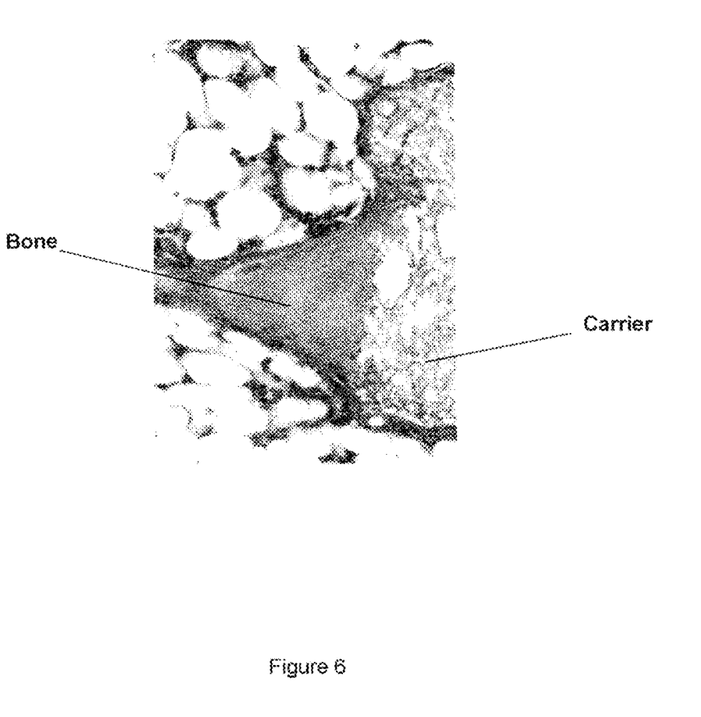
FIG. 6 illustrates the histological appearance of the new bone (Bone) formed on a carrier (Carrier) when bioimplant produced according to the method of the invention was implanted into a mouse

Backscatter SEM showed that by 28 days bone formed throughout the bioimplant and onto the calcium phosphate particulate that had been incorporated into the PLGA (FIG. 5). Histology confirmed the tissue formed was bone (FIG. 6).

Example 9: An In Vivo Assay for Release of BMPs from Bioimplants

The present example describes how to measure the release of rhBMP-2 from the various bioimplants described in Examples 1, 2, 3, 4 or 5 following implantation into an animal. Methods to do this are well known in the art. For example see Uludag et al. J Biomed Mater Res, 46, 193-202, 1999.

Materials & Methods

Recombinant hBMP-2 is radiolabeled with Iodine125 (1-125) by Perkin Elmer. The radiolabelled rhBMP-2 (hot) is mixed with unlabeled rhBMP-2 (cold) to produce a hot cold mixture of 1:100.

Bioimplants containing known amounts of rhBMP-2 are prepared as in Examples 1 to 5. These bioimplants are then implanted into animals as described in Example 8. At various times the animals are sacrificed and the implant site is dissected out. The dissected tissue is then weighed, and the amount of radioactivity determined using a gamma counter.

To determine whether the counts are associated with protein, the tissue is homogenized in 0.5 ml PBS+0.5% BSA. Two mls of ice cold 10% trichloroacetic acid are added to the homogenate and is then held for at least 1 hour at 4° C. The homogenate is then centrifuged and the supernatant removed. The radioactivity of the precipitate is then measured using a gamma counter.

The radioactivity associated with implants is corrected for the decay and the total amount of BMP remaining in the implant is estimated.

Example 10: Production of a Carrier with a Short Sustained Release Profile

The present example describes means of producing a carrier that releases a growth factor with a short sustained release profile.

Materials & Methods

Macroporous biphasic calcium phosphate (BCP) granules (Eclipse) were purchased from Citagenix (Laval, Qc, Canada.) Recombinant human BMP-2 (rhBMP-2, Induce Biologics Inc) was prepared in formulation buffer (1.5 mg/ml, pH 4.5; 5 mm glutamic acid, 2.5% glycine, 0.5% sucrose and 0.01% Tween™ 80 with ddH2O).

Sterile rhBMP-2 solution was incubated with sterile BCP granules at a ratio of 9.1 µg per 5 mg or 4.55 µg per 5 mg (BMP per BCP) for 15 minutes under shaking. The samples were then frozen and lyophilized aseptically.

Following lyophilization the carriers were weighed into 5 mg aliquots and placed in sterile epindorf tubes. Some tubes had 33% F127 (45.5 µl added). The BMP release profile was then determined as described in Example 6.

Results

Figure 7:
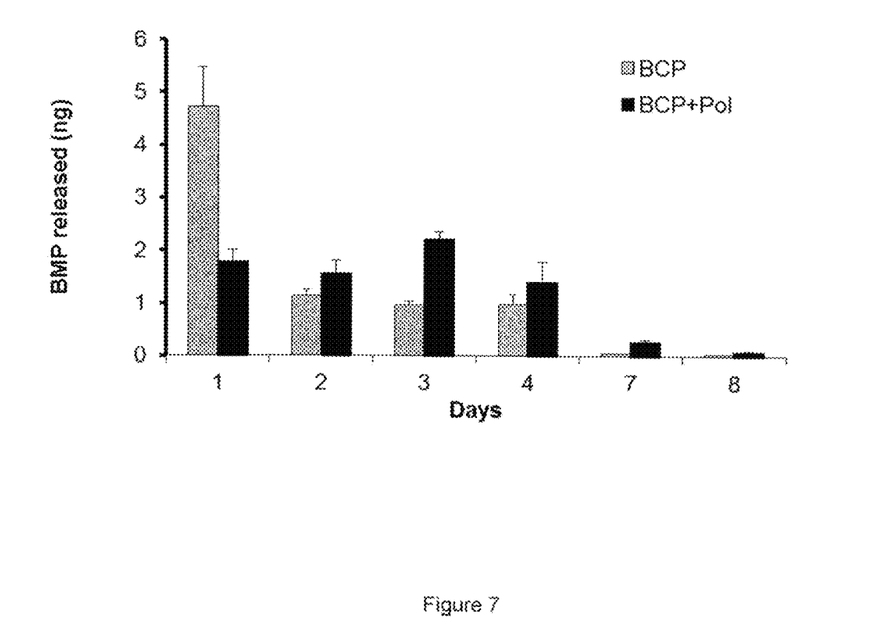
FIG. 7 illustrates a short sustained growth factor release profile produced by a carrier produced according to the method of the invention

Carriers that were not coated with F127 (BCP) showed a burst release profile with the largest amount of BMP released over the first day and then decreasing amounts of BMP released at each subsequent time point. Mixing the BCP within the F127 (BCP-Pol) resulted in a short sustained release profile where similar amount of BMP were collected each day over the first 4 days (FIG. 7).

Example 11: Altering the Sustained Release Profile of the Carrier

The present example describes a means of altering the release profile from a carrier.

Materials & Methods

PLGA with differing inherent viscosities and molecular weights were purchased from Birmingham Polymers Inc. (Birmingham, Ala.). Carriers were then made using these PLGAs as described in Example 1. The BMP release profile from these carriers was determine according to the method of Example 6.

Results

Figure 8:
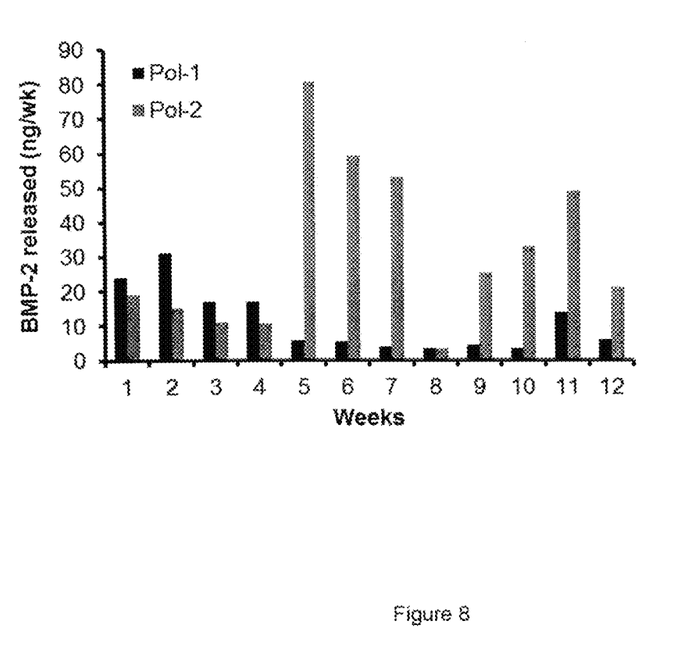
FIG. 8 illustrates how a sustained release profile can be altered by changing the properties of the carrier produced according to the method of the invention

All carriers produced sustained release profiles. However the amount of BMP released differed depending on the viscosity/molecular weight of the PLGA used. The carriers made with low viscosity PLGA (Pol-1) released more rhBMP-2 than those using the high viscosity (Pol-2) PLGA over the 12 week duration of the study (FIG. 8).

What is claimed is:

1. A composition for multiphasic release of growth factors at a treatment site, the composition comprising:
   a delivery vehicle comprising at least one first growth factor; and
   a carrier comprising at least one second growth factor;
wherein:
   the delivery vehicle is a polymer liquid or gel that is in a flowable form to be applied on the carrier and adapted to release about 80% of the at least one first growth factor within a first time period of 72 hours; and, the carrier consists of a plurality of calcium phosphate particles that are adapted to release the at least one second growth factor in a sustained release profile over a second time period.

2. The composition according to claim 1, wherein the polymer gel is formed from poloxamer 407.

3. The composition according to claim 1, wherein the first time period comprises several hours or days and wherein the second time period comprises several days or weeks.

4. The composition according to claim 1, wherein the at least one first growth factor and the at least one second growth factor are the same or different and at least one of the first and second growth factors is chosen from: growth factors of the transforming growth factor beta superfamily; insulin-like growth factors (IGFs); fibroblast growth factors (FGFs); platelet derived growth factors (PDGFs); and vascular endothelial growth factors (VEGFs).

5. The composition according to claim 1, wherein the at least one second growth factor is BMP-2 or BMP-7.

6. The composition according to claim 1, wherein the delivery vehicle delivers at least 10% of the total amount of the at least one first growth factor and the carrier delivers at least 50% of the total amount of the at least one second growth factor.

7. The composition according to claim 1, wherein the plurality of particles is dispersed within a polymeric matrix.

8. The composition according to claim 7, wherein the polymeric matrix comprises polylactic acid (PLA) or polylactic-co-glycolic acid (PLGA).

9. The composition according to claim 1, wherein the at least one second growth factor of the carrier is provided on the surfaces of the particles or is mixed within the particles.

10. The composition of claim 1, wherein the delivery vehicle comprises a reverse phase polymer.

11. The composition of claim 1, wherein the composition comprising the delivery vehicle and the carrier is in the form of a gel or putty when the carrier is mixed within the delivery vehicle.

12. The composition of claim 1, wherein the ratio of the carrier to the delivery vehicle is from 1:1 to 2:1 (v/v).

13. A kit for multiphasic delivery of growth factors, the kit comprising:
a delivery vehicle component;
at least one first growth factor associated with the delivery vehicle and adapted to be delivered by the delivery vehicle;
a carrier component; and
at least one second growth factor associated with the carrier and adapted to be delivered by the carrier;
wherein:
the delivery vehicle is a polymer liquid or gel that is in a flowable form to be applied on the carrier and adapted to release about 80% of the at least one first growth factor within a first time period of 72 hours; and
the carrier consists of a plurality of calcium phosphate particles that are adapted to release the at least one second growth factor in a sustained release profile over a second time period.

14. The kit according to claim 13, wherein the at least one second growth factors is BMP-2 or BMP-7.

15. The kit according to claim 13, wherein the at least one first growth factor comprises at least 10% of the total amount of growth factors provided in the kit and the at least one second growth factor comprises at least 50% of the total amount of growth factors provided in the kit.

16. The kit according to claim 13, wherein the first time period comprises several hours or days and wherein the second time period comprises several days or weeks.

17. The kit according to claim 13, wherein the plurality of particles is dispersed within a polymeric matrix.

18. The kit according to claim 13, wherein the at least one second growth factor of the carrier is provided on the surfaces of the particles or is mixed within the particles.

19. The kit according to claim 13, wherein:
the at least one first growth factor and the at least one second growth factor are the same or different and at least one of the first and second growth factors is chosen from: growth factors of the transforming growth factor beta superfamily; insulin-like growth factors (IGFs); fibroblast growth factors (FGFs); platelet derived growth factors (PDGFs); and vascular endothelial growth factors (VEGFs).

20. The kit according to claim 13, wherein the at least one second growth factor is BMP-2 or BMP-7.

21. The kit of claim 13, wherein the delivery vehicle comprises a reverse phase polymer.

* * * * *